United States Patent
Zimpfer

(10) Patent No.: US 8,164,929 B2
(45) Date of Patent: Apr. 24, 2012

(54) CONTROLLED CONTACTLESS POWER TRANSMISSION

(75) Inventor: Arno Zimpfer, Mammendorf (DE)

(73) Assignee: Schleifring und Apparatebau GmbH, Furstenfeldbruck (DE)

( * ) Notice: Subject to any disclaimer, the term of this patent is extended or adjusted under 35 U.S.C. 154(b) by 393 days.

(21) Appl. No.: 12/542,499

(22) Filed: Aug. 17, 2009

(65) Prior Publication Data

US 2011/0038190 A1 Feb. 17, 2011

(51) Int. Cl.
  *H02M 5/40* (2006.01)
  *H02J 3/00* (2006.01)
(52) U.S. Cl. .................. 363/34; 378/4; 378/15
(58) Field of Classification Search .............. 363/34, 363/126; 378/4, 15, 101, 104, 107, 109–114
  See application file for complete search history.

(56) References Cited

U.S. PATENT DOCUMENTS

| | | | |
|---|---|---|---|
| 4,969,171 A * | 11/1990 | Yamada et al. | 378/101 |
| 6,351,626 B1 | 2/2002 | Lohr | |
| 6,442,434 B1 | 8/2002 | Zarinetchi et al. | |
| 6,515,878 B1 | 2/2003 | Meins et al. | |
| 6,674,836 B2 * | 1/2004 | Harada et al. | 378/107 |
| 6,975,698 B2 * | 12/2005 | Katcha et al. | 378/15 |
| 7,054,411 B2 | 5/2006 | Katcha et al. | |
| 7,197,113 B1 | 3/2007 | Katcha et al. | |
| 2007/0195924 A1 | 8/2007 | Krumme | |
| 2007/0223256 A1 * | 9/2007 | Kidokoro et al. | 363/34 |
| 2008/0310201 A1 * | 12/2008 | Maksimovic | 363/85 |
| 2009/0276199 A1 | 11/2009 | Krumme et al. | |

FOREIGN PATENT DOCUMENTS

| | | |
|---|---|---|
| DE | 102005020186 | 11/2006 |
| JP | 2003159242 | 6/2003 |
| JP | 2004080844 | 3/2004 |

* cited by examiner

*Primary Examiner* — Adolf Berhane
*Assistant Examiner* — Emily Pham
(74) *Attorney, Agent, or Firm* — Meyertons, Hood, Kivlin, Kowert & Goetzel, P.C.; Eric B. Meyertons

(57) ABSTRACT

An inductive coupled power transmission circuit has a rotating transformer, including an AC voltage supply for feeding an AC voltage via a series capacitor into the primary winding of said rotating transformer and a load being coupled to the secondary winding of said rotating transformer. The AC voltage supply includes a line rectifier for receiving AC voltage from a power line and generating a DC voltage. This is fed into a DC/DC converter for converting the DC voltage from the line rectifier into a controlled intermediate DC voltage. An AC generator generates an AC voltage from the intermediate DC voltage and feeds this via a matching transformer into the primary winding of the rotating transformer. A measuring circuit measures voltages and/or currents within the AC voltage supply and a function generator estimates voltage and/or current values at the load based on the measured values and controls the DC/DC converter and/or the AC generator based on the estimated values.

8 Claims, 2 Drawing Sheets

CONTROLLED CONTACTLESS POWER TRANSMISSION

BACKGROUND OF THE INVENTION

1. Field of the Invention

The invention relates to a contactless power transmission system for transmission of power between a rotating part and a stationary part, in particular between a rotating part and a stationary part of a computer tomograph, and also to a method for transmitting power via a rotating power transmission device.

2. Description of the Relevant Art

With rotating units such as radar units or also computer tomographs, and also with linearly movable units such as crane and conveyor units, it is necessary to transmit electrical power between units that are movable relative to each other.

Non-contacting inductive rotary joints are an advantageous substitute for the known mechanical slip-rings for transmission of electrical energy. In inductive transmission technology a coupling between rotatable units is effected with magnetic fields without contact. This has an advantage over mechanical slip-rings in that torque, wear, and maintenance are minimized. Furthermore, the surroundings of the rotary joints are not polluted by carbon dust.

Inductive rotary joints, as disclosed in U.S. Pat. No. 7,197,113 have at least one winding on each of the rotatable units. Furthermore, an iron core or ferrite core for concentrating the magnetic field may be provided on the rotor as well as on the stator, or also on both parts. An alternating current signal is fed into a winding of one of the parts while another winding on the other part feeds a load.

With a conductively coupled slip-ring a constant voltage can be easily transferred from a constant voltage power supply at the stationary side to a load at the rotating side. Due to the conductive connection of low ohmic resistance through the slip-ring, the output voltage will correspond to the input voltage, except for minor deviations. Owing to the low resistance of the slipping, a low and usually negligible voltage drop depending on the load current is obtained.

At inductively coupled rotary joints an equivalent circuit diagram of the transmission device includes a stray inductance as a series inductance between the input side and the load side. This results in a series reactance between input and load. This stray inductance depends on the intrinsic inductance of the joint and, in particular, on the coupling factor. Especially with inductive rotary joints of large dimensions, it is often possible to obtain only a small coupling factor which, in addition, frequently fluctuates with the positions of the rotatable units relative to each other. Thus, for example, the coupling factor decreases with increase of an air-gap between the iron cores that are rotatable relative to each other. The stray inductance and accordingly its series reactance then increase accordingly. This leads to significant changes in load voltage. Furthermore with a lower coupling factor changes of the load resistance result in stronger changes of load voltage.

In order to transmit higher power via the rotary joint despite this stray inductance, the stray inductance is used in suitable circuits like a discrete inductance. Its use would be, for example, as a storage inductance, or also as a resonance inductance. In the case of a resonance inductance, the inductance can be supplemented for example with a series capacity to form a series resonance circuit, or with a parallel capacity to form a parallel resonance circuit. Of course, more complex resonating structures also may be obtained. A rotary transmission device of this kind having resonance circuits is disclosed for example in the International patent application publication WO 98/32217 A1. One of the most serious problems in such resonance circuits is the energy stored in the resonance elements e.g. the inductance and the capacitance. This energy makes a quick control or change of the output parameters (Voltage, Current) very difficult. If the output voltage should be lowered then first the energy from the resonance circuit must be discharged. Otherwise before increasing the output voltage, energy must be charged into the resonance circuit. Another problem is that a data link is required for feedback of the measured output voltage to the primary side.

In order to achieve constant supply to the output side, and to prevent a destruction of the connected components, it is necessary to control at least one of the electrical parameters on the output side. For low power transmission, a separate controller such as a voltage controller that is constructed to be a series regulator or also a switching controller may be used at the output side. For higher power, at least one sensor for at least one of these electrical parameters should be provided on the output side. This sensor determines the magnitude of this electrical parameter and signals it to the alternating signal source on the input side. Now another electrical parameter such as for example current, voltage or also the frequency on the input side can be controlled with a control amplifier so that the electrical parameter at the output side is kept constant. A technology of this kind is known for conventional switching power supplies and is also regularly applied and disclosed in U.S. Pat. No. 7,054,411. With rotary joints there is the problem that information from a sensor must be transmitted from the output side to the input side, i.e. between two units that are rotatable relative to each other. This requires a further rotary joint operating in an opposite transmission direction from that of the inductive power transmitter. However, often no mechanical construction space is available for an additional rotary joint. This may also increase costs.

The problems presented here increase with increase of size of the rotary joint. Thus, with compact units having diameters of a few centimeters it is still possible to use precise bearings with tolerances below 0.1 mm. With this, it is possible to achieve, for example, a precise air-gap of 0.2 mm, and a fluctuation during rotation in a range of 0.2 mm to 0.3 mm. With large units having diameters larger than 1 meter, as used for example in computer tomographs, the tolerances are already in a range of a few millimeters, and are partly greater than 5 mm. Thus, in a case like this the air-gap would vary between 1 and 6 mm, depending on position and operating conditions. This leads to a substantially larger stray inductance which, in addition, fluctuates substantially more strongly.

Another problem is control of the power delivered through the rotating transformer. Prior art uses AC generators fed by the AC line voltage as it is supplied by a power line. To control the power to be delivered to the load, the frequency of the AC generator is controlled. Maximum power can be transferred at the resonance frequency of the rotating transformer and its resonance capacitor. At lower or higher frequencies the power transfer is reduced. The problem is that with lower transferred power the reactive power and therefore the reactive currents in the circuit increase. Furthermore switching of currents which are out of phase with voltage as they occur at frequencies off the resonance frequency is difficult and leads to higher power losses in the switching circuit.

SUMMARY OF THE INVENTION

The following description of various embodiments of systems and methods utilizing rotating data transmission devices is not to be construed in any way as limiting the subject matter of the appended claims.

The disadvantages of the prior art may be overcome by a rotary joint designed for non-contacting inductive transmission of electrical power having a constant output voltage or current so that a feedback from an output side sensor to an alternating current source on an input side is no longer needed. Furthermore it should have increased control capabilities of output power and reduced switching losses.

Achievements of this object in accordance with the invention are set out in the independent patent claims. Further developments of the invention form the subject matter of the dependent claims.

This objective is achieved with a rotating power transmission device having a transformer like design for transmission of electrical power between a first part and a second part, of which one of the parts is a rotating part and the other part is a stationary part, with the first part including a primary winding and the second part including a secondary winding. Furthermore magnetic cores including iron or ferrite materials are provided to control the magnetic field between primary and secondary winding.

The primary winding is coupled via a series capacitor to an AC voltage supply for generating a controlled AC voltage. The secondary winding is coupled to a load like an X-Ray tube. The series capacitor forms together with the inductance of the rotating transformer a resonance circuit having a preferred resonance frequency, further referred to as the resonance frequency. Furthermore an additional inductor may be provided in series with the series capacitor to lower the resonance frequency of the circuit.

The inventive AC voltage supply is designed to deliver a controlled output voltage at a controlled frequency and is adapted to the impedance of the rotating transformer and the load. It includes a DC power supply stage which generates a stable intermediate DC voltage from a rectified AC power line voltage. This DC power supply stage may be a boost converter, a Cuk converter or any other suitable converter. Preferably this converter is controlled by a circuit to have a comparatively high AC line input power factor, like a PFC (Power Factor Control). The AC voltage supply further includes an AC generator, e.g. an inverter circuit to generate an AC voltage from the stable DC voltage. It preferably is a full bridge or half bridge circuit. To adapt the AC voltage supply to the load impedance, preferably a matching transformer is provided. This inventive AC voltage supply has an output voltage which can easily be controlled by simply adjusting the intermediate DC voltage, supplied by the DC/DC converter. As the frequency of the AC generator can always be adjusted to its optimum operating point, close to the resonance frequency of the resonance circuit which includes the series capacitors and the inductance of the rotating transformer, it runs at its optimum efficiency. Therefore switching losses are minimized. Furthermore a measuring circuit for measuring voltages and/or currents within the AC voltage supply is provided. A function generator estimates voltage and/or current values at the load based on the measured values and controls the DC/DC converter and/or the AC generator based on the estimated voltage and/or current values to keep the load current or voltage constant.

The above objective is also achieved by a method for transmitting power via a rotating power transmission device, including: converting voltage from a power line to a controlled intermediate DC voltage, further converting this intermediate DC voltage into an AC voltage and transferring that AC voltage via a rotating transformer.

BRIEF DESCRIPTION OF THE DRAWINGS

In the following, the invention will be described by way of example, without limitation of the general inventive concept, on examples of embodiment and with reference to the drawings.

Figure 1:
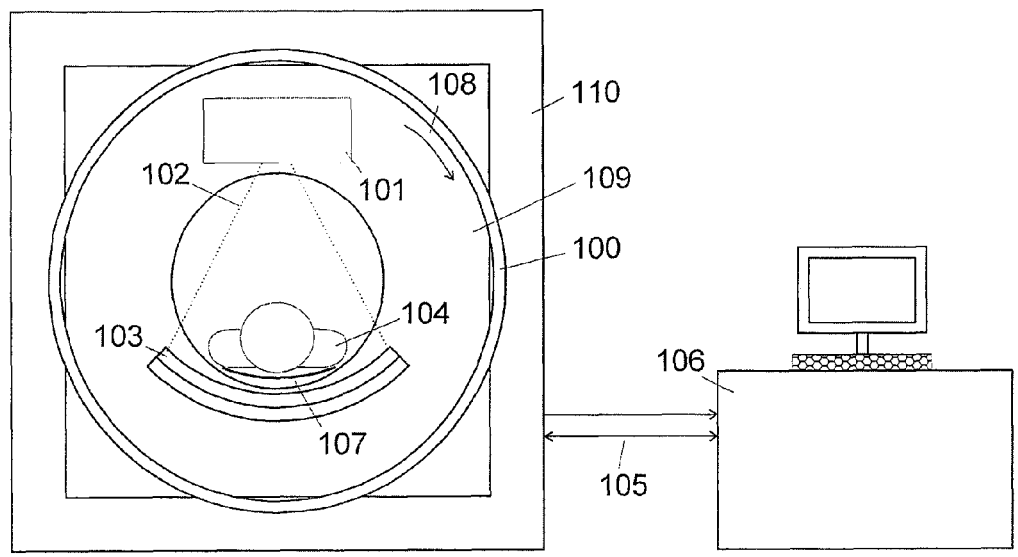
FIG. 1 schematically shows in a general form a computer tomograph.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE DRAWINGS

FIG. 1 shows a computer tomograph in which an example of a rotating data transmission device is used. The computer tomograph (CT scanner) includes two mechanical main parts. A stationary part 110 serves as a base and support for the entire instrument in which a rotating part 109 rotates. A patient 104 is positioned on a bed 107 in an opening of the rotating part. An X-ray tube 101 and also a detector 103 disposed oppositely thereto are provided for scanning the patient by means of X-rays 102. The X-ray tube 101 and the detector 103 are disposed to be rotatable on the rotating part 109. A rotating transformer 100 serves as an electrical connection between the rotating part 109 and the stationary part 110. An evaluation and control unit 106 serves for operating the computer tomograph and also for displaying the generated images. Communication with the computer tomograph is effected via a data link 105.

Figure 2:
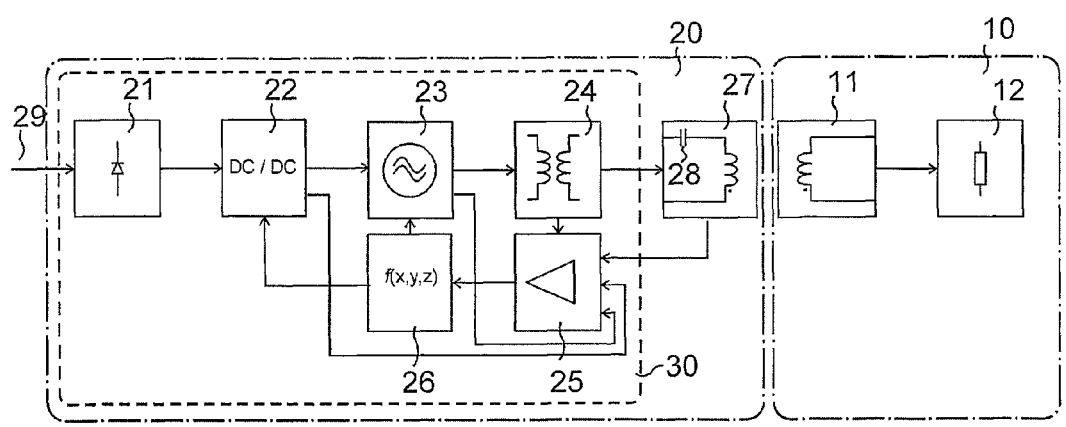
FIG. 2 schematically shows a power transmission incorporated into the computer tomograph illustrated in FIG. 1.

FIG. 2 shows in a simplified form an example of an arrangement of a power transmission system The stationary part 20 is coupled via a rotating transformer including a primary side 27 and a secondary side 11 to the rotating part 10. The stationary part 20 receives input power from the power line input 29. This may be a 3 phase AC input e.g. 3*400V AC/50 Hz. This input is rectified by the line rectifier 21. After the rectifier there may be some filtering capacitors to reduce the ripple of the rectified input signal. This rectified input signal is converted to an intermediate DC voltage by the DC/DC converter 22. This DC/DC converter typically is a boost converter transforming the input voltage into a higher output voltage. This converter is preferably controlled by an internal control circuit to have an input current consumption synchronized to the power line voltage thus resulting in a comparatively high power factor. Such a circuit may also be called a power factor correction circuit. The AC generator 23 produces an AC voltage from the intermediate DC voltage. This AC generator basically includes a switching stage, like a full bridge circuit. Basically the amplitude of the AC voltage is a function of the intermediate DC voltage and can be controlled by controlling the intermediate DC voltage. For adapting the output impedance and the output voltage/current level a matching transformer 24 is provided. A further advantage of the matching transformer is the isolation between primary and secondary winding. Due to this isolation the common mode signals which are coupled over the rotating transformer from the stationary to the rotating parts can be reduced. If this isolation is not required, an autotransformer may be used, resulting in smaller size and lower costs. At the secondary side of the transformer there is the primary side of the rotating transformer 27 together with a series capacitor 28. The inductance, more specifically the stray inductance of the rotating transformer forms a resonance circuit together with the series capacitor 28. The circuit has a plurality of resonance frequencies, but there is only one series resonance frequency, at which the circuit provides a very low series resistance from the primary side to the secondary side and is therefore able to transfer high current from the primary side of the rotational transformer to the secondary side. Dependent on the load 12 at the secondary side of the rotating transformer 11 the intermediate DC voltage of the DC/DC converter 22 or the frequency of the AC generator 23 is selected to achieve the necessary power throughput over the rotating transformer. A measuring circuit 25 measures voltages and/or currents at the matching transformer 24 and/or the primary side of the rotating transformer 27. The measured values coupled to the function generator 26 which generates an estimate of current and/or voltage at the load 12. Derived from these estimates are control signals to control the DC/DC converter 22 and/or the AC generator 23 four supplying a constant voltage or a constant current to the load 12. Furthermore the function generator 26 may be coupled to receive current and/or voltage values from DC/DC converter 22. As the AC generator 23 is almost running at the resonance frequency of the resonance circuit, the AC generator 23 together with its matching transformer 24 and the rotating transformer has a comparatively high efficiency, which is independent of the load in a wide load range. As explained before, due to the operation of the circuit at the resonance frequency, the output voltage is a function of the DC intermediate voltage. Due to the high efficiency also the output current is a function of the current supplied by the DC/DC converter into the AC generator. Accordingly measurement or at least estimation of current and/or voltage at the load can easily buy done by measuring voltage and/or current at the DC/DC converter. The function generator is generating the appropriate control signals from these measured values to set the DC/DC converter to produce the necessary DC intermediate voltage. The function generator may further generate control signals to precisely control the frequency of the AC generator 23.

Figure 3:
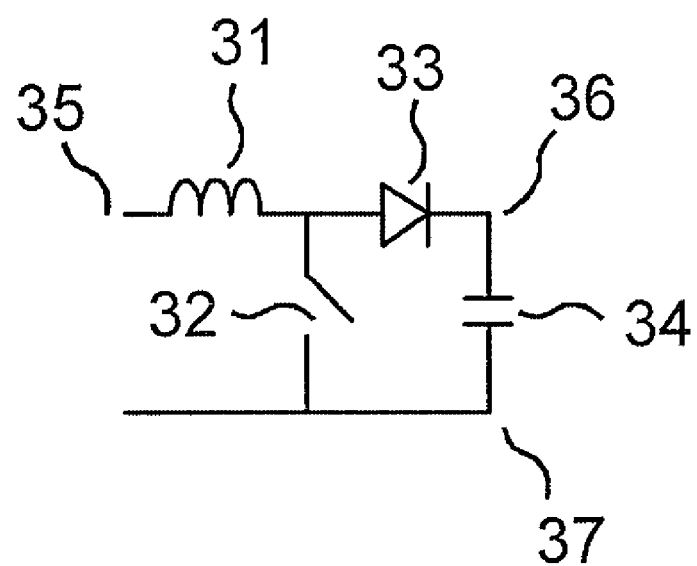
FIG. 3 schematically shows a DC/DC converter.

FIG. 3 shows the basic diagram of a DC/DC converter constructed as a boost converter. It has a series inductor 31 connected from the input 35 of the DC/DC converter to a semiconductor switch 32 for switching the series inductor to ground 37 in specified time intervals. The output voltage 36 is coupled from the series inductor to an output capacitor 34 via a diode 33.

DETAILED DESCRIPTION OF THE PREFERRED EMBODIMENTS

In a preferred embodiment output voltage and output current of the DC/DC converter 22 are measured to estimate voltage and current at the load 12. As an alternative input voltage and/or current thereof are measured. Specifically the output values of the DC/DC converter 22 are easy to measure as the output is a DC voltage and a corresponding DC current. By using these measured values new set point values for the DC/DC converter are calculated by the function generator 26.

In a further embodiment the matching transformer has a shield between primary and secondary windings. This further helps to reduce suppression of common mode currents. This shield may be a foil or a winding.

A further embodiment relates to the DC/DC converter 22. It preferably includes a cascaded control circuit, including a first high-speed current control loop and a second low speed voltage control loop defining the set point for the first control loop.

In another embodiment the DC/DC converter 22 is a boost converter and includes a PID control loop for controlling its output voltage which has a proportional, an integral and a differential component. According to the standard boost converter circuit it has a series inductor 31 connected from the input 35 of the DC/DC converter to a semiconductor switch 32 for grounding the series inductor in specified time intervals. The proportional and integral components of the control loop signals are derived from the intermediate DC voltage as delivered from the output of the DC/DC converter 22. The differential component is calculated as the difference of the DC/DC converter's output current and the current through the series inductor. This value is proportional to the differentiated value of the voltage difference. The advantage is that it can be easily measured, requires no computing time for differentiating and has a comparatively good signal to noise ratio.

In a further embodiment the active current at the output of the AC generator 23 is measured by the measuring circuit 25 and delivered to the function generator 26 for calculating the load current and/or voltage.

In a further preferred embodiment the output current of the AC generator 23 is sampled by a digital sampling circuit either in the measuring circuit 25 or the function generator 26 and multiplied with the polarity of the AC generator control signal defining the output polarity of the AC signal. This signal may have a logic one value if the AC generator output voltage is positive and a logic zero value if the AC generator output voltage is negative. Now the sampled output current signal is multiplied by 1, if the control signal has a logic one value and by −1, if the control signal has a logic zero value. Polarity of signals may also be changed.

In another embodiment the rotating power transmission device is disposed for power transmission between a rotating part and a stationary part of a computer tomograph.

It will be appreciated to those skilled in the art having the benefit of this disclosure that this invention is believed to provide systems and methods utilizing rotating data transmission devices. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. Inductive coupled power transmission circuit having a rotating transformer, comprising
    an AC voltage supply for feeding an AC voltage via a series capacitor into the primary winding of said rotating transformer and a load being coupled to the secondary winding of said rotating transformer, wherein said AC voltage supply comprises a line rectifier for receiving AC voltage from a power line and generating a DC voltage;

a DC/DC converter for converting the DC voltage from the line rectifier into a controlled intermediate DC voltage;

an AC generator for generating said AC voltage from said intermediate DC voltage;

a matching transformer being connected to said AC generator and said primary winding of the rotating transformer for matching impedance and voltage levels;

a measuring circuit for measuring voltages and/or currents within the AC voltage supply; and a function generator for estimating voltage and/or current values at the load based on the measured values and for controlling the DC/DC converter and/or the AC generator based on the estimated voltage and/or current values to keep the load current or voltage constant.

2. Inductive coupled power transmission circuit according to claim 1, wherein the measuring circuit measures output voltage and output current of the DC/DC converter and estimates current and/or a voltage at the load thereof.

3. Inductive coupled power transmission circuit according to claim 1, wherein the matching transformer has an electrical shield between its primary and secondary windings.

4. Inductive coupled power transmission circuit according to claim 1, wherein the DC/DC converter comprises a cascaded control circuit, comprising a first high-speed current control loop and a second low speed voltage control loop defining the set point for the first control loop.

5. Inductive coupled power transmission circuit according to claim 1, wherein the DC/DC converter is a boost converter having an inductor and comprises a PID control loop for controlling its output voltage which has a proportional, an integral and a differential component, and the proportional and integral components of the control loop signals are derived from the intermediate DC voltage as delivered from the output of the DC/DC converter, while the differential component is calculated as the difference of the DC/DC converter's output current and the current through the series inductor.

6. Inductive coupled power transmission circuit according to claim 1, wherein the active current at the output of the AC generator is measured by the measuring circuit and delivered to the function generator for calculating the load current and/or voltage.

7. Inductive coupled power transmission circuit according to claim 6, wherein the output current of the AC generator is sampled by a digital sampling circuit either in the measuring circuit or the function generator and multiplied with the polarity of the AC generator control signal defining the output polarity of the AC signal.

8. Inductive coupled power transmission circuit according to claim 1, being disposed for power transmission between a rotating part and a stationary part of a computer tomograph.

* * * * *

UNITED STATES PATENT AND TRADEMARK OFFICE
CERTIFICATE OF CORRECTION

| | | |
|---|---|---|
| PATENT NO. | : 8,164,929 B2 | Page 1 of 1 |
| APPLICATION NO. | : 12/542499 | |
| DATED | : April 24, 2012 | |
| INVENTOR(S) | : Arno Zimpfer | |

It is certified that error appears in the above-identified patent and that said Letters Patent is hereby corrected as shown below:

In the Claims:

Claim 5, col. 8, line 12, please delete "the series inductor" and substitute therefor -- the inductor --.

Signed and Sealed this
Fourteenth Day of August, 2012

David J. Kappos
*Director of the United States Patent and Trademark Office*